United States Patent
Biedermann et al.

(10) Patent No.: US 11,298,157 B2
(45) Date of Patent: Apr. 12, 2022

(54) CLOSURE ASSEMBLY FOR SECURING A STABILIZATION ELEMENT IN A RECEIVING PART OF A BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 8 days.

(21) Appl. No.: 16/856,839

(22) Filed: Apr. 23, 2020

(65) Prior Publication Data

US 2020/0337737 A1    Oct. 29, 2020

Related U.S. Application Data

(60) Provisional application No. 62/839,203, filed on Apr. 26, 2019.

(30) Foreign Application Priority Data

Apr. 26, 2019   (EP) ..................... 19171415

(51) Int. Cl.
| | | |
|---|---|---|
| A61B 17/70 | (2006.01) | |
| A61B 17/68 | (2006.01) | |
| A61B 17/86 | (2006.01) | |

(52) U.S. Cl.
CPC ........ *A61B 17/7037* (2013.01); *A61B 17/683* (2013.01); *A61B 17/7032* (2013.01); *A61B 17/863* (2013.01); *A61B 17/8605* (2013.01)

(58) Field of Classification Search
CPC .................. A61B 17/70; A61B 17/7032–7046
See application file for complete search history.

(56) References Cited

U.S. PATENT DOCUMENTS

| | | |
|---|---|---|
| 5,005,562 A | 4/1991 | Cotrel |
| 5,534,001 A | 7/1996 | Schlapfer et al. |
| | (Continued) | |

OTHER PUBLICATIONS

Extended European Search Report for Application No. 19171415.3, dated Oct. 16, 2019, 10 pages.

*Primary Examiner* — Eduardo C Robert
*Assistant Examiner* — Michelle C Eckman
(74) *Attorney, Agent, or Firm* — Lewis Roca Rothgerber Christie LLP (57) ABSTRACT

A closure assembly for securing an elongate stabilization element in a receiving part of a bone anchoring device includes a first closure member and a second closure member. The first closure member is receivable between legs of the receiving part, has an axis of rotation, and includes an outer surface with an engagement portion configured to engage the legs of the receiving part, and an inner surface having at least a portion that is threaded and that defines a central passage that passes axially through the first closure member. The second closure member has an axis of rotation and an outer surface having a threaded portion configured to cooperate with the threaded portion of the inner surface of the first closure member. The threaded portion of the outer surface of the second closure member includes a multi-start thread with at least two starts.

20 Claims, 8 Drawing Sheets

(56) References Cited

U.S. PATENT DOCUMENTS

| | | |
|---|---|---|
| 6,224,598 B1 | 5/2001 | Jackson |
| 8,828,060 B2 | 9/2014 | Biedermann et al. |
| 9,636,146 B2* | 5/2017 | Jackson ............... A61B 17/863 |
| 2009/0163956 A1* | 6/2009 | Biedermann ...... A61B 17/7037 606/265 |
| 2013/0103093 A1* | 4/2013 | Biedermann ...... A61B 17/8685 606/272 |
| 2013/0218213 A1 | 8/2013 | Lemoine |
| 2014/0081334 A1 | 3/2014 | Jackson et al. |
| 2014/0142633 A1* | 5/2014 | Jackson ............... A61B 17/683 606/273 |

* cited by examiner

CLOSURE ASSEMBLY FOR SECURING A STABILIZATION ELEMENT IN A RECEIVING PART OF A BONE ANCHORING DEVICE

CROSS-REFERENCE TO RELATED APPLICATION(S)

The present application claims priority to and the benefit of U.S. Provisional Patent Application No. 62/839,203, filed Apr. 26, 2019, the contents of which are hereby incorporated by reference in their entirety, and claims priority from European Patent Application EP 19 171 415.3, filed Apr. 26, 2019, the contents of which are hereby incorporated by reference in their entirety.

BACKGROUND

Field

The application relates to a closure assembly for securing a stabilization element in a receiving part of a bone anchoring device, and to a bone anchoring device including such a closure assembly. In particular, embodiments of the invention are applicable in orthopaedic surgery and more specifically in orthopaedic spinal surgery.

Description of Related Art

In orthopaedic spinal surgery, pedicle screws and rods are often used to stabilize spinal segments. The pedicle screws are bone anchoring devices that include a shank for anchoring in bone and a receiving part for coupling a stabilizing rod to the shank. The shank may be polyaxially connected to the receiving part in a so-called polyaxial bone anchoring device, or may be fixedly connected to the receiving part in a so-called monoaxial bone anchoring device, where usually in the latter the shank and the receiving part form a zero angle. Various closure assemblies are known to capture and lock the rod in the receiving part and to lock an angular position of a shank that is pivotably connected to the receiving part.

Two part closure assemblies are well known, for example, from U.S. Pat. No. 6,224,598 B1 for a monoaxial bone anchoring device and U.S. Pat. No. 8,828,060 B2 for a polyaxial bone anchoring device. On the other hand, various single part closure devices are known, such as from U.S. Pat. No. 5,005,562 or again from U.S. Pat. No. 8,828,060 B2.

Specifically, U.S. Pat. No. 9,636,146 B2 proposes a single part cylindrical closure member that comprises first and second helically wound thread forms located on the closure member, the first helically wound thread form having a first start and a second helically wound thread form having a second start that cooperate with a first helically wound thread form on the first arm of the receiver member and a second helically wound thread form on the second arm of the receiver member opposite the first helically wound thread form.

SUMMARY

While various closure assemblies are described in the prior art that try to overcome drawbacks resulting from force distribution and transfer during screwing in or tightening of the closure assembly, there is still a need for an improved closure assembly used in connection with bone anchoring devices for the stabilization of vertebrae or bone parts.

Hence, it is an object of the invention to provide an improved closure assembly and a bone anchoring device with such a closure assembly that provides a still better force distribution and locking force generated by the closure assembly.

According to an aspect, a closure assembly for securing an elongate stabilization member in a receiving part of a bone anchoring device includes a first closure member having an axis of rotation and an outer surface, a central passage located in and passing axially through the first closure member, an internal surface of the passage including an internal thread on at least a portion thereof, wherein the first closure member is configured to be received between a pair of legs of a receiving part of a bone anchoring device, and a second closure member having an axis of rotation and an outer surface including an external thread configured to cooperate with the internal thread of the first closure member, wherein the external thread includes a multi-start thread including at least two starts.

By means of the multi-start thread the force resulting from the screwing of the second closure member relative to the first closure member is distributed not only to one thread, but to at least two or more threads. As a result, force can be transferred more evenly to the first closure member. Also, possible splaying or twisting of the legs during locking of the head of the bone anchoring element may be further reduced.

According to another aspect, the thread form of the multi-start thread is a flat thread. With the flat thread, the force distribution can be further improved.

According to another aspect, the first closure member includes an external thread which is configured to cooperate with an internal thread provided on the inner surface of the legs of the receiving part. The external thread of the first closure member and the internal thread of the receiving part may be single-start threads. Moreover, the thread form of the external thread of the first closure member and the internal thread of the receiving part may be different. For example, the thread form of the external thread may be a flat thread and the thread form of the internal thread may be a trapezoidal thread, a buttress thread, a helical flange thread, a negative angle thread, or another thread form that is sized and shaped to cooperate with the flat external thread of the first closure member. This permits use of the closure assembly with various types of receiving parts that differ in terms of the internal threads provided on the legs.

The drive portions of the first closure member and the second closure member may have various shapes so as to fit to an instrument used to insert and tighten the closure assembly.

According to a still further aspect, a bone anchoring device includes a shank for anchoring in bone and a receiving part connected to the shank, wherein the receiving part is substantially cylindrical and includes a substantially U-shaped recess forming two legs for receiving an elongate stabilization element therebetween. The bone anchoring device further includes the closure assembly. When the shank is pivotably connectable to the receiving part, the closure assembly may be configured such that the first closure member is adapted to lock an angular position of the receiving part relative to the shank and the second closure member is adapted to lock the elongate stabilization member in the recess. A pressure member or pressure element may be further provided in the receiving part to exert pressure onto a head which forms an end portion of the shank. The pressure element may be configured to selectively receive rods of different diameters.

In combination with closure assemblies in accordance with various embodiments of the invention, a variety of bone anchoring devices may be assembled with only a small number of basic parts.

BRIEF DESCRIPTION OF THE DRAWINGS

Further features and advantages of the invention will become apparent from the description of embodiments, by means of the accompanying drawings. In the drawings:

FIG. 6 shows a perspective view from a top of a first closure member of the first embodiment of the closure assembly shown in FIGS. 1 to 3 and 5a.

FIG. 9 shows a perspective view from a top of a second closure member of the first embodiment of the closure assembly shown in FIGS. 1 to 3 and 5a.

DETAILED DESCRIPTION

Figure 1:
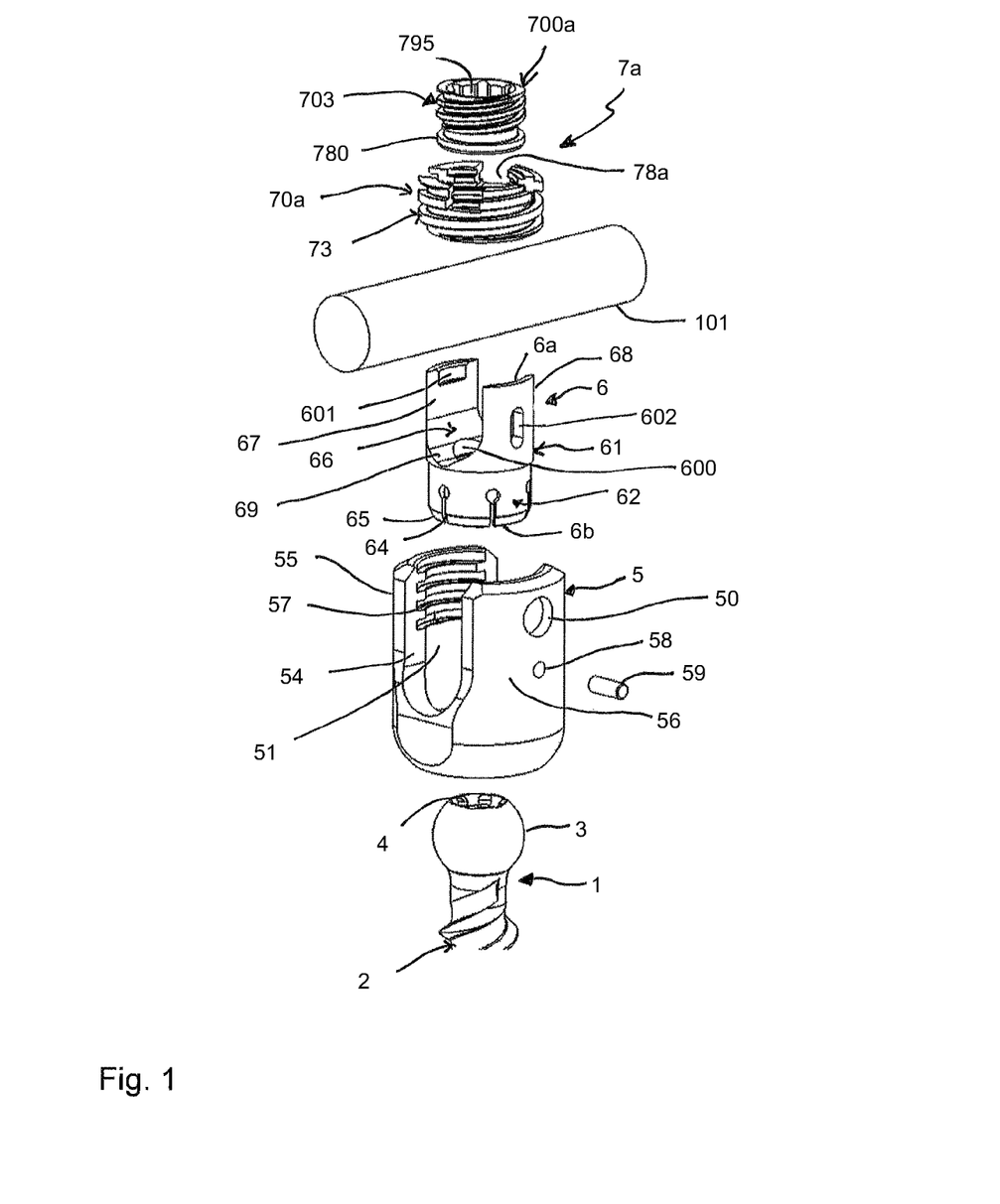
FIG. 1 shows a perspective exploded view of an embodiment of a bone anchoring device with a first embodiment of a closure assembly.
Figure 2:
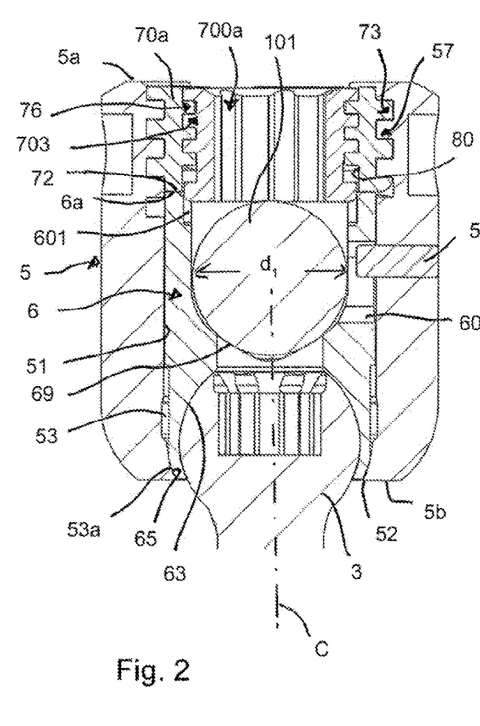
FIG. 2 shows a cross-sectional view of the bone anchoring device and closure assembly of FIG. 1 in an assembled state, wherein the cross-section is taken in a plane extending through a center of the legs of the receiving part and perpendicular to a rod axis of a first rod having a first diameter.
Figure 3:
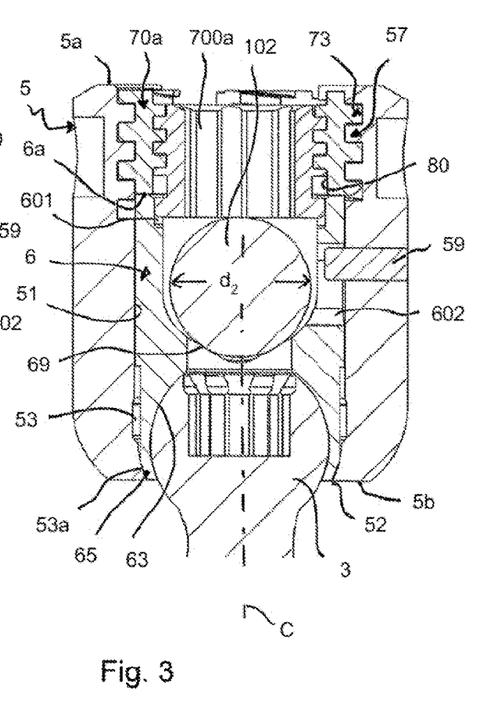
FIG. 3 shows a cross-sectional view of the bone anchoring device and closure assembly of FIG. 1 in an assembled state, wherein the cross-section is taken in a plane extending through a center of the legs of the receiving part and perpendicular to a rod axis of a second rod having a second diameter.

A bone anchoring device including a closure assembly according to a first embodiment will be described with reference to FIGS. 1 to 3. The bone anchoring device includes a bone anchoring element 1 having a shank 2 with a threaded portion and a head 3. The head 3 has a spherically-shaped outer surface portion and, on its side opposite to the shank 2, a recess 4 for engagement with a tool. A receiving part 5 is provided for coupling the bone anchoring element 1 to an elongate fixation member such as a first rod 101 having a diameter $d_1$ or to a second rod 102 having a diameter $d_2$ that may be smaller than $d_1$. In the receiving part 5, a pressure element 6 is arranged to exert pressure onto the head 3 of the bone anchoring element 1.

Additionally, the bone anchoring device includes a closure assembly 7a. The closure assembly 7a includes a first or outer closure member 70a and a second or inner closure member 700a. The first closure member 70a and the second closure member 700a are configured to capture one of the rods 101, 102 in the receiving part 5. Furthermore, the first closure member 70a and the second closure member 700a are configured to lock the receiving part 5 relative to the shank 2 and relative to the first rod 101 or the second rod 102 in an independent manner.

The receiving part 5 has a first or top end 5a and a second or bottom end 5b opposite to the top end 5a. The receiving part 5 may have a substantially cylindrical outer shape with a longitudinal axis C extending through the top end 5a and the bottom end 5b. Coaxially with the longitudinal axis C, a passage 51 is provided extending from the top end 5a to the bottom end 5b and forming an opening 52 at the bottom end 5b. At a distance from the top end 5a, the passage 51 widens into an accommodation space 53 that is configured to receive the head 3 and at least a portion of the pressure element 6. Adjacent to the opening 52 at the bottom end 5b, the accommodation space 53 narrows towards the opening 52 in a narrowing portion 53a. The narrowing portion 53a may be, for example, a tapered surface, and in particular a conical surface that may cooperate with a corresponding portion of the pressure element 6. The width of the opening 52 may be greater than the greatest width of the head 3, so that the head 3 may be inserted from the bottom end 5b into the accommodation space 53. To enable the insertion of the head 3 from the bottom end 5b, the width of the accommodation space 53 is such that the pressure element 6 can expand therein to permit the insertion of the head 3, as explained in greater detail below.

The receiving part 5 further has a substantially U-shaped recess 54 formed at the top end 5a and extending in the direction of the bottom end 5b. By means of the U-shaped recess 54, two free legs 55, 56 are formed and define a channel that is open towards the first end 5a for receiving the first rod 101 or the second rod 102 therein.

On an inner surface of the legs 55, 56, an inner or internal thread 57 is formed. As depicted in the figures, the internal thread 57 is in the exemplary embodiment a square thread or another form of a flat thread. In cross-section, the flat thread includes a plurality of thread ridges 570 separated from one another by a root 571 of the internal thread, each thread ridge 570 including a first or upper flank facing towards the top end 5a and an opposite second or lower flank facing towards the bottom end 5b of the receiving part 5, wherein the upper flank and the lower flank each forms an angle of substantially 90° with the central axis C. A cross-section of the thread ridges 570 is substantially rectangular, or, as shown in the exemplary embodiment, is substantially square-shaped. Preferably, the internal thread 57 is a single-start thread. In the exemplary embodiment, the internal thread 57 ends at a distance from the upper end without a thread run-out or an undercut.

Moreover, a transverse hole 58 may extend through one of the legs 55, 56, in a direction perpendicular to the central axis C and at a position approximately at the center of the legs 55, 56 in a circumferential direction. The transverse hole 58 may serve for accommodating a pin 59 that extends through the hole into the passage 51. The pin 59 is configured to engage the pressure element 6 to secure the pressure element 6 against rotation. In addition, the pin 59 may limit an upward movement of the pressure element 6. At an upper portion of the legs 55, 56, substantially at the center in a circumferential direction, recesses 50 may further be formed for engagement with a tool.

The pressure element 6 may be formed as a monolithic part, with a first or upper end 6a and a second or lower end 6b opposite to the upper end 6a. Adjacent to the upper end 6a, the pressure element has a substantially cylindrical first portion 61 with an outer diameter that is only slightly smaller than an inner diameter of the passage 51 so that the first portion 61 can be received in the passage 51 and moved therein in an axial direction. Adjacent to the lower end 6b, a second substantially cylindrical portion 62 is formed that is configured to extend at least partially into the accommodation space 53 of the receiving part 5. The second portion 62 may have a slightly smaller outer width compared to the first portion 61. Adjacent to the lower end 6b, a substantially spherical segment-shaped recess 63 is formed in the second portion 62, which is designed and sized so as to frictionally hold therein the head 3 of the bone anchoring element 1. A plurality of longitudinal slits 64 that are open to the lower end 6b are provided that extend into the wall of the second portion 62 and render the second portion 62 flexible. Adjacent to the lower end 6b, the outer surface of the second portion 62 includes a narrowing portion 65, preferably a tapered and more preferably a conically tapered portion that is configured to cooperate with the narrowing portion 53a of the accommodation space 53. By means of the cooperating surfaces 65, 53a of the pressure element 6 and of the receiving part 5, respectively, the flexible second portion 62 of the pressure element 6 can be compressed to clamp or lock the head 3 therein.

Adjacent to the upper end 6a, a recess 66 forms two open legs 67, 68 that preferably have opposite flat inner walls and a base 69. The base 69 has a substantially V-shaped contour when viewed along a direction perpendicular to the central axis C. The distance between the inner sidewalls of the recess 66 and an angle of the V-shape of the base 69 is such that at least the first rod 101 having the first diameter $d_1$ and the second rod 102 having the second diameter $d_2$ can be received in the recess 66. More generally, the recess 66 is shaped and sized such that a rod with a largest diameter and a rod with a smallest diameter can be inserted and contact the base 69 at substantially two contact lines. The depth of the recess 66 may be such that for all the rods having a diameter between the smallest and the largest diameter, the legs 67, 68 extend above the upper surface of the inserted rod.

Moreover, the pressure element 6 includes a coaxial bore 600 that serves for accessing the recess 4 of the head 3 with a tool. In addition, two opposite recesses 601 may be formed in the inner wall of the legs 67, 68 that extend from the upper end 6a towards the base 69. The recesses 601 may be sized and shaped so as to permit a portion of the second closure member 700a to extend therein. At approximately the center of one of the legs 67, 68 in a circumferential direction, the leg has an axially elongate hole 602 that is configured to be engaged by the pin 59. The cooperation between the pin 59 and the elongate hole 602 prevents rotation of the pressure element 6 in the receiving part 5. Furthermore, the pin 59 forms a stop against an upward movement of the pressure element 6 when the head 3 is inserted through the lower opening 52 of the receiving part into the recess 63 of the pressure element 6.

Referring additionally to FIGS. 5a and 6 to 11, the closure assembly 7a according to the first embodiment will be described. The first closure member 70a has an axis of rotation R and a central passage 70 located in and passing axially through the first closure member 70a. Between a first or upper end 71 and an opposite second or lower end 72, a substantially cylindrical outer surface extends, with an external thread 73 provided on at least a portion of the outer surface. The external thread is configured to cooperate with the internal thread 57 of the legs 55, 56. In other words, the first closure member 70a includes a nut which can be screwed in between the legs 55, 56 of the receiving part 5.

Figure 4:
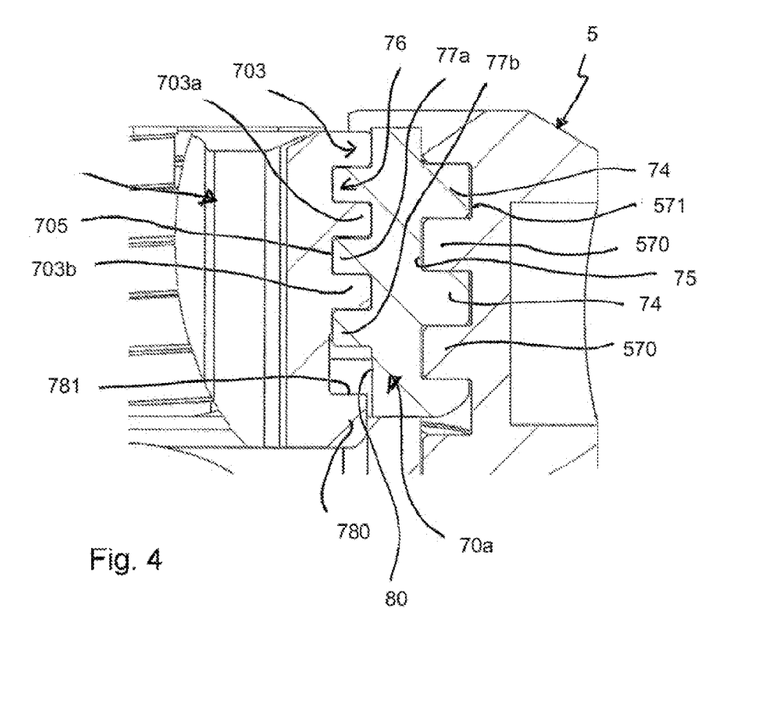
FIG. 4 shows a cross-sectional view of an enlarged portion of FIG. 2.

In the exemplary embodiment, the external thread 73 is a flat thread. As depicted in greater detail in FIG. 4, in cross-section, the external thread 73 includes a plurality of uniform thread ridges 74 that are separated by a root 75 of the external thread. Each thread ridge 74 includes an upper flank facing towards the upper end 71 and an opposite lower flank facing towards the lower end 72, wherein the upper and lower flanks each form an angle with the axis of rotation R that is substantially 90°. A cross-section of the external thread 73 may be substantially rectangular, and more preferably square-shaped. Moreover, the external thread 73 is preferably a single-start thread.

The first closure member 70a further includes an inner surface which is provided with an inner or internal thread 76. The internal thread 76 is preferably a multi-start thread, in the exemplary embodiment a double-start thread. In cross-section, internal thread 76 includes one or more uniform first thread ridges 77a forming a first thread with a first thread start or thread entry and one or more uniform second thread ridges 77b forming a second thread with a second thread entry and running between the first thread ridges 77a. Each of the first and second threads are formed as flat threads in the exemplary embodiment. Hence, each of the upper and lower flanks of the thread ridges 77a, 77b forms an angle of substantially 90° with the axis of rotation R, and cross-sections of each of the thread ridges 77a, 77b may be substantially rectangular or preferably square. The thread entries may be spaced apart from one another at the upper end 71 by 180° in the circumferential direction. As can be seen in particular in FIGS. 2 and 3, a depth of the first and second threads may be smaller than a depth of the internal thread 57 of the receiving part 5.

The internal thread 76 may extend up to a distance from the lower end 72, so that a thread free surface portion 80 may be provided adjacent to the lower end 72.

Finally, the first closure member 70a includes adjacent to the upper end 71 an engagement structure for engagement with an instrument that is configured to rotate and advance the first closure member 70a between the legs 55, 56 of the receiving part 5. In the exemplary embodiment, the engagement structure has at least two, preferably a plurality, for example, four, equally spaced recesses 78a. The recesses 78a are open to the upper end 71 and extend to a distance therefrom. Moreover, the recesses 78a extend entirely through the first closure member 70a in a radial direction, from the outer surface to the inner surface. A contour of the recesses may be, for example, rectangular.

The second closure member 700a may be a set screw that is configured to be screwed into the first closure member 70a. Hence, the second closure member 700a has an axis of rotation R that coincides in the mounted state with the axis of rotation R of the first closure member 70a, and an outer substantially cylindrical surface. An upper end 701 and an opposite lower end 702 define the orientation of the second closure member 700a. In the mounted state, the orientation is such that the upper end 701 is positioned at or near a same side as the upper end 71 of the first closure member and the lower end 702 is positioned at or near a same side as the lower end 72 of the first closure member 70a.

An external thread 703 is provided on the outer surface of the second closure member 700a, and may be a multi-start thread, where in the exemplary embodiment, external thread 703 is formed as a double-start thread. In greater detail, when viewed in cross-section, the external thread 703 includes a first thread having first uniform thread ridges 703a separated from each other by a root 705 of the external thread or threads, and having a first thread entry 704, and second thread ridges 703b arranged between the first thread ridges 703a and having a second thread entry 707. As can be seen in particular in FIG. 9, the first thread entry 704 and the second thread entry 707 are spaced apart by substantially 180° in the circumferential direction. Corresponding to the internal thread 76 of the first closure member 70a, the external thread 703 may be formed as a flat thread. Each of the thread ridges 703a, 703b includes an upper flank which faces towards the upper end 701 and a lower flank which faces towards the lower end 702, wherein the upper and the lower flanks form an angle of substantially 90° with the axis of rotation R and the cross-section of each of the ridges is substantially rectangular, more preferably square-shaped. Generally, the external thread 703 of the second closure member 700a is configured to mate and cooperate with the internal thread 76 of the first closure member 70a.

Figure 10:
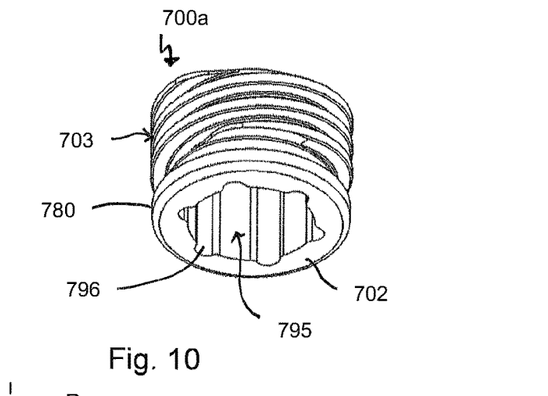
FIG. 10 shows a perspective view from a bottom of the second closure member of FIG. 9.
Figure 11:
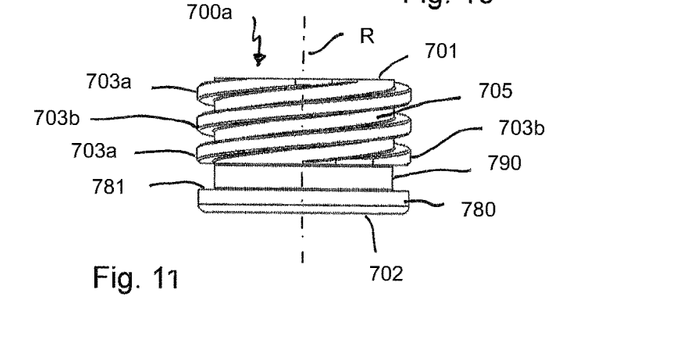
FIG. 11 shows a side view of the second closure member of FIGS. 9 and 10.
Figure 12:
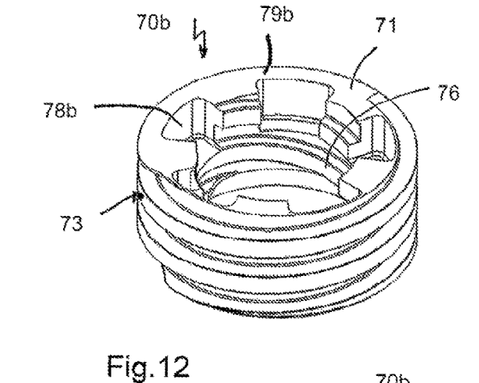
FIG. 12 shows a perspective view from a top of a first closure member of a second embodiment of the closure assembly shown in FIG. 5b.
Figure 13:
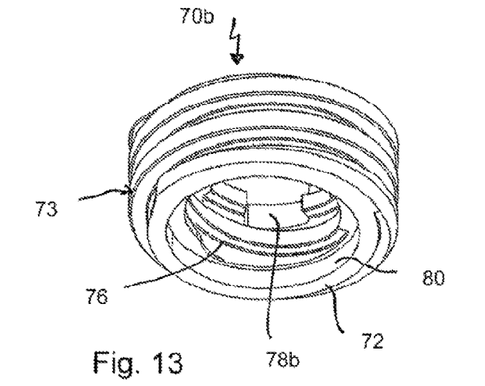
FIG. 13 shows a perspective view from a bottom of the first closure member of FIG. 12.
Figure 14:
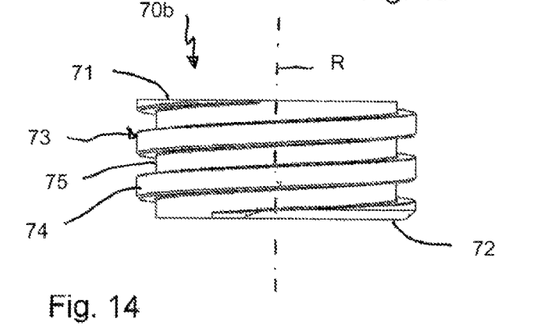
FIG. 14 shows a side view of the first closure member of FIGS. 12 and 13.
Figure 15:
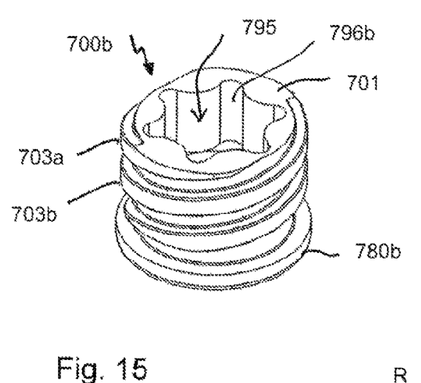
FIG. 15 shows a perspective view from a top of a second closure member of the second embodiment of the closure assembly shown in FIG. 5b.
Figure 16:
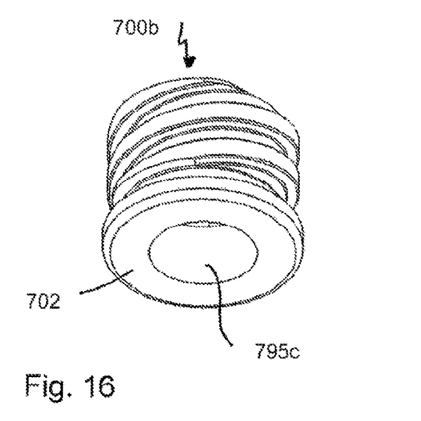
FIG. 16 shows a perspective view from a bottom of the second closure member of FIG. 15.
Figure 17:
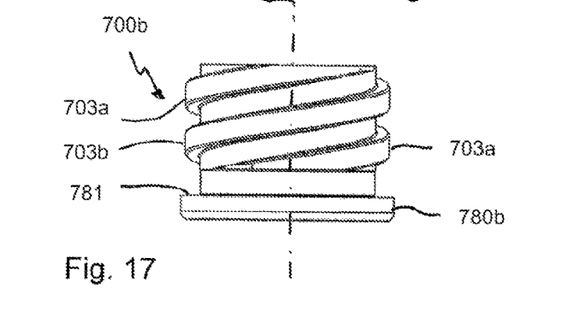
FIG. 17 shows a side view of the second closure member of FIGS. 15 and 16.
Figure 18:
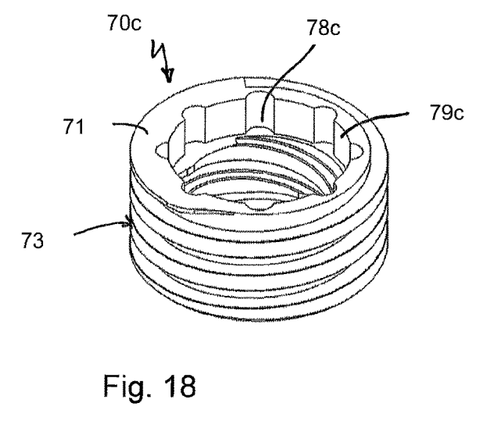
FIG. 18 shows a perspective view from a top of a first closure member of a third embodiment of the closure assembly shown in FIG. 5c.
Figure 19:
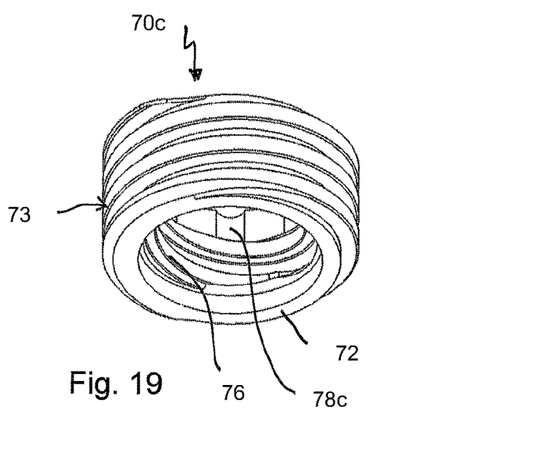
FIG. 19 shows a perspective view from a bottom of the first closure member of FIG. 18.

As can be seen in particular in FIG. 10, the external thread 703 extends from the upper end 701 to a distance from the lower end 702. Adjacent to the lower end 702, an annular rim 780 is formed, the outer diameter of which may be substantially equal to the major or outer thread diameter of the external thread 703. Between the annular rim 780 and the external thread, a thread-free surface 790 may be provided. The annular rim 780 has an upper surface 781 that faces towards the upper end 701 and that may be perpendicular to the axis of rotation R. Thereby, the upper surface 781 provides an abutment when it touches the lowermost thread turn of the internal thread 76 of the first closure member 70a in an assembled configuration. This prevents inadvertent screwing out of the second closure member 700a through the upper end 71 of the first closure member 70a when the closure assembly is in a mounted state in the receiving part 5.

Lastly, the second closure member 700a includes a coaxial passage 795 that extends entirely through the second closure member 700a from the upper end 701 to the lower end 702. An engagement structure is provided at an inner wall of the passage 795, which may be formed by a substantially polygonally-shaped inner contour of the passage 795 with rounded longitudinal grooves 796 at the edges or corners of the polygon.

The closure assembly 7a is assembled by screwing the second closure member 700a from the lower end 72 into the first closure member 70a until the upper surface 781 of the annular rim 780 abuts against the lowermost thread turn of the internal thread 76 of the first closure member 70a. The closure assembly may be used in a preassembled configuration.

Turning again to FIGS. 1 to 3, the first rod 101 and the second rod 102 may have a circular cross-section along their entire lengths. Alternatively, one or both of the rods may have a circular cross-section only in certain sections, for example, in sections of the rod that are configured to be received in the receiving part 5. The first rod 101 and the second rod 102 may have a size such that they are rotatable around the rod axis and/or displaceable in the channel formed by the recess 54, and in particular by the recess 66 of the pressure element.

The parts and elements of the bone anchoring device, including the closure assembly, may be made of preferably bio-compatible materials, for example, of titanium or stainless steel, of a bio-compatible alloy, such as NiTi-alloys, for example Nitinol, of magnesium or magnesium alloys, and/or from a bio-compatible plastic material, such as, for example, polyether ether ketone (PEEK) or poly-L-lactide acid (PLLA). The parts can be made of the same as or of different materials from one another.

In use, the receiving part 5 may be preassembled with the pressure element 6 held in the receiving part via the pin 59. The receiving part 5 with pressure element 6 may then be coupled to the bone anchoring element 1 by inserting the head 3 through the opening 52 into the recess 63 of the pressure element 6. When the head 3 enters into the recess 63, the pressure element 6 is moved upwards in the passage 51 until further upward movement is limited by the pin 59. The flexible second portion 62 of the pressure element 6 expands in the accommodation space 53 and snaps onto the head 3. The pressure element 6 may then be pressed down so that the cooperating surfaces 53a of the receiving parts 5 and 65 of the pressure element 6 engage to preliminarily hold the head 3 in the receiving part in a pivotable manner.

To connect two bone anchoring devices inserted into bone parts or vertebrae, one of the first rod 101 or the second rod 102 is selected and inserted into each of the receiving parts 5 until the rod rests on the base 69. To lock the angular position of the receiving part 5 relative to the shank 2 and to fix a position of the inserted rod 101, 102, the closure assembly 7a is inserted into the receiving part 5 from the upper end 5a. The first closure member 70a is screwed down until its lower end 72 presses onto the upper end 6a of the pressure element 6. Tightening the first closure member 70a locks the angular position of the head 3, and thereby the shank 2, relative to the receiving part 5. Thereafter, the second closure member 700a is screwed down until its lower end 702 contacts the inserted first rod 101 or second rod 102. Tightening the second closure member 700a fixes the position of the inserted rod. It shall also be noted that the position of the rod 101, 102 can first be fixed by tightening the second closure member 700a, and thereafter the angular position of the head 3 can be locked by tightening the first closure member 70a.

Loosening of the locking of the head 3 or the fixation of the rod 101, 102 can also be effected independently. This allows carrying out of various correction and adjustment steps in a repeatable manner.

When the second closure member 700a exerts pressure onto the rod, the counterforce experienced by the second closure member 700a is distributed via the multi-start external thread 703, more specifically by the double-start external thread to the first closure member 70a, more evenly. This positively influences the force distribution between the second closure member 700a and the first closure member 70a and/or between the first closure member 70a and the legs 55, 56 of the receiving part 5.

Turning now to FIGS. 5b and 12 to 17, a second embodiment of the closure assembly will be described. Parts and portions that are identical or similar to those of the first embodiment are reflected using the same reference numerals, and the descriptions thereof will not be repeated. The second embodiment 7b of the closure assembly includes a first closure member 70b and a second closure member 700b. The first closure member 70b differs from the first closure member 70a of the first embodiment by the engagement structure and the shape of the upper end 71. The engagement recesses 78b in this exemplary embodiment are open towards the upper end 71 and towards the inner surface of the first closure member 70b, but are closed towards the outer surface of the first closure member 70b. By means of this, an annular wall 79b remains and extends around an outside of the first closure member 70b. In the exemplary embodiment shown, there are more than four engagement recesses 78b (e.g., five recesses), and the recesses each has a slightly increasing width towards the upper end 71 to facilitate engagement with a tool. Also, the internal thread 76 of the first closure member 70b may have a different size in terms of thread diameter, pitch, etc. compared to the first embodiment.

The second closure member 700b differs from the second closure member of the first embodiment in that the engagement recess 796b has a different shape, for example, a torx-shape or star-like shape. Furthermore, the engagement recess 796b extends only to a distance from the lower end 702. The passage adjacent to the lower end 702 may be formed as a coaxial bore 795c. The annular rim 780b may have an outer diameter exceeding that of the major or outer thread diameter of the external thread 703. Correspondingly, each of the thread-free surface 80 of the first closure member 70b and the recesses 601 of the pressure element 6 may also have an enlarged inner diameter to accommodate the larger annular rim 780b.

A third exemplary embodiment of the closure assembly will be described with reference to FIGS. 18 to 21. The first closure member 70c differs from the first closure member of the second embodiment in that the engagement structure has a substantially polygon-shaped recess with longitudinal grooves 78c formed in the inner surface of the first closure member 70c, leaving a thick annular wall portion 79c, the outer surface of which forms part of the outer surface of the first closure member 70c. This may enhance the stability of the first closure member 70c.

Figure 20:
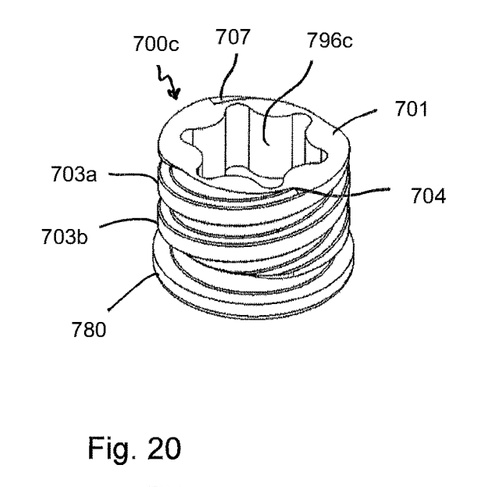
FIG. 20 shows a perspective view from a top of a second closure member of the third embodiment of the closure assembly shown in FIG. 5c.
Figure 21:
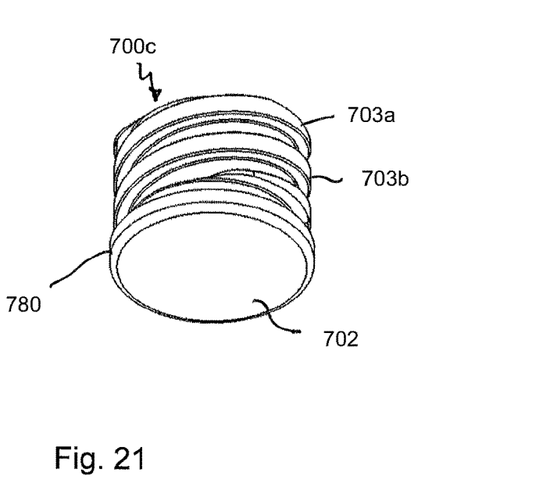
FIG. 21 shows a perspective view from a bottom of the second closure member of FIG. 20.

The second closure member 700c differs from the second closure member of the second embodiment in that the second closure member 700c is closed at the lower end 702. The engagement recess 796c extends to a distance from the upper end 701. The remainder of the second closure member 700c is a solid body.

Figures 5A, 5B:
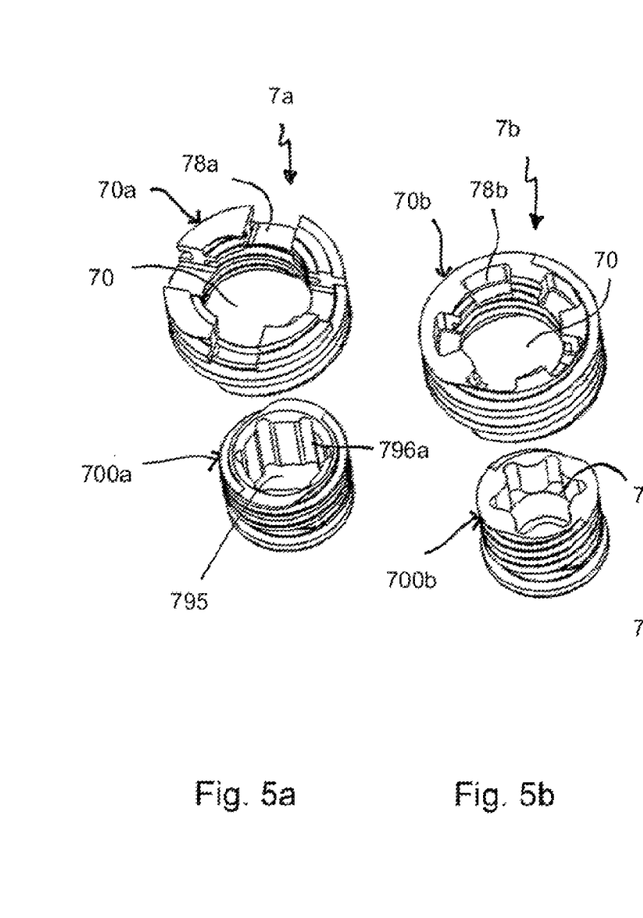
FIGS. 5a to 5e show perspective exploded views of various embodiments of the closure assembly.
Figure 5C:
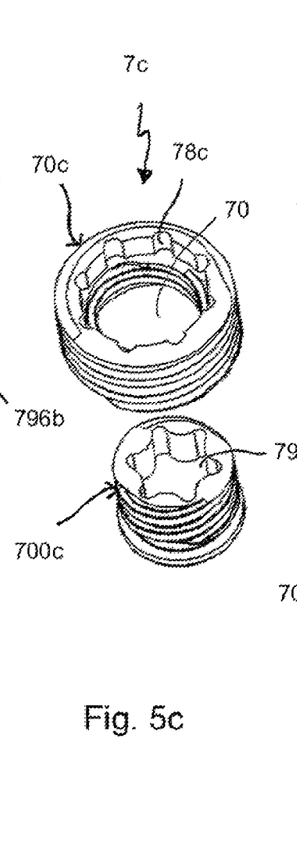
Figures 5D, 5E:
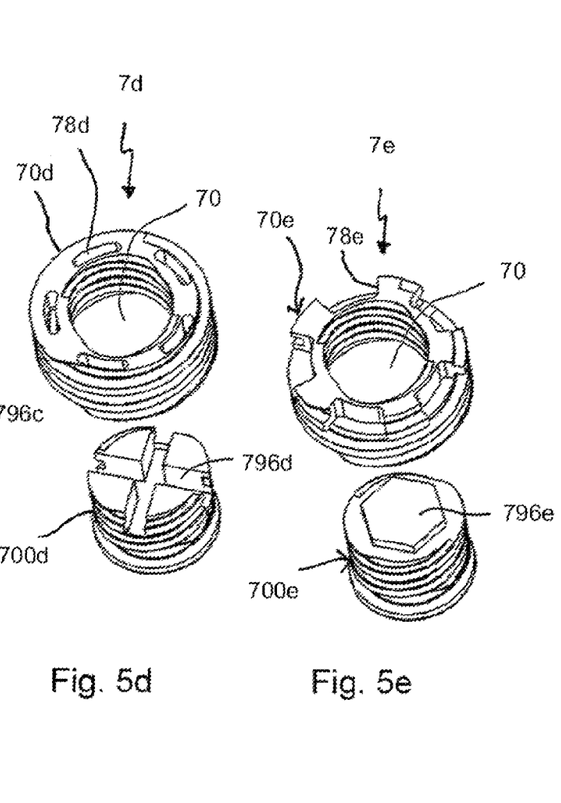
Figure 6:
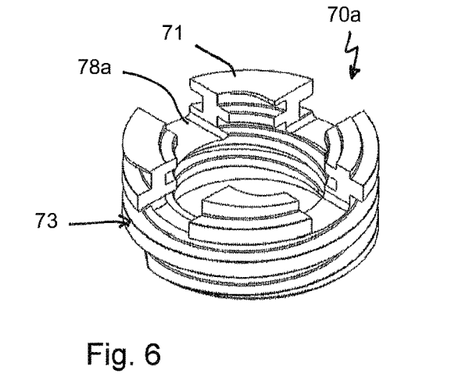
Figure 7:
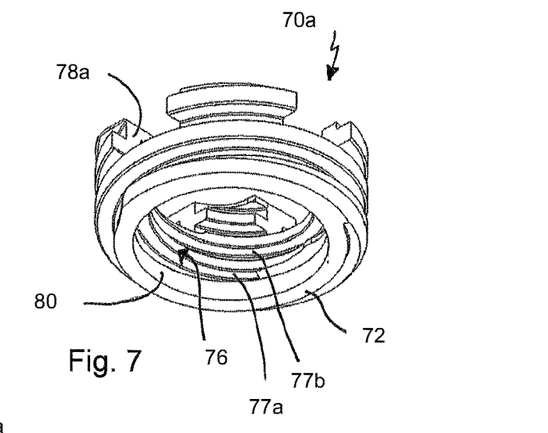
FIG. 7 show a perspective view from a bottom of the first closure member of FIG. 6.
Figure 8:
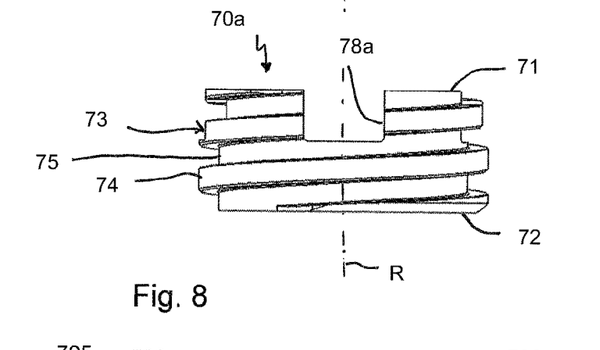
FIG. 8 shows a side view of the first closure member of FIGS. 6 and 7.
Figure 9:
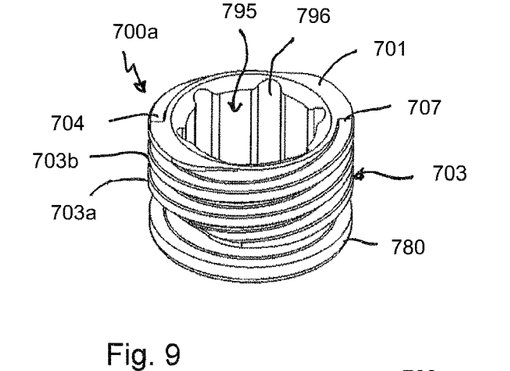
Figure 22:
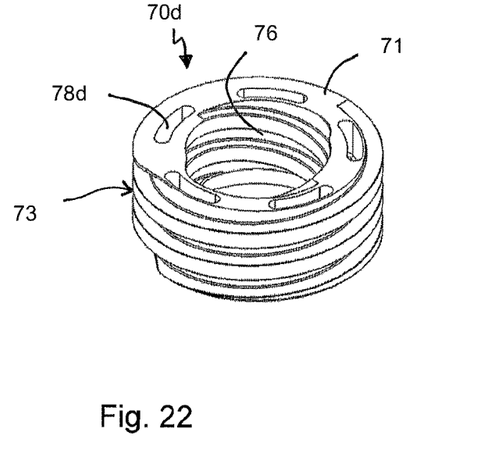
FIG. 22 shows a perspective view from a top of a first closure member of a fourth embodiment of the closure assembly shown in FIG. 5d.
Figure 23:
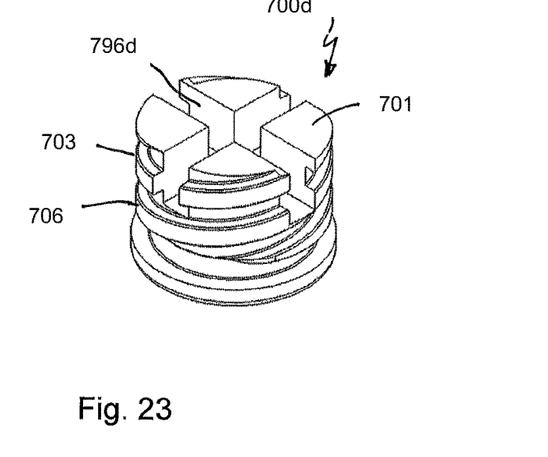
FIG. 23 shows a perspective view from a top of a second closure member of the fourth embodiment of the closure assembly shown in FIG. 5d.
Figure 24:
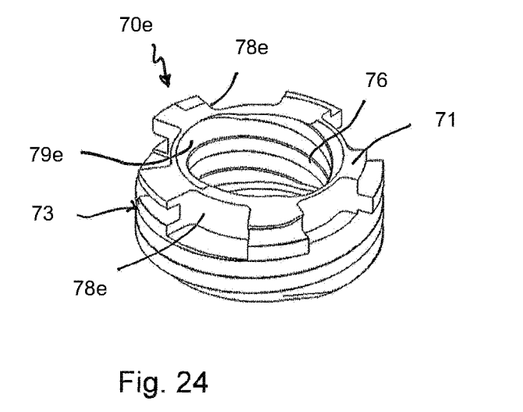
FIG. 24 shows a perspective view from a top of a first closure member of a fifth embodiment of the closure assembly shown in FIG. 5e.
Figure 25:
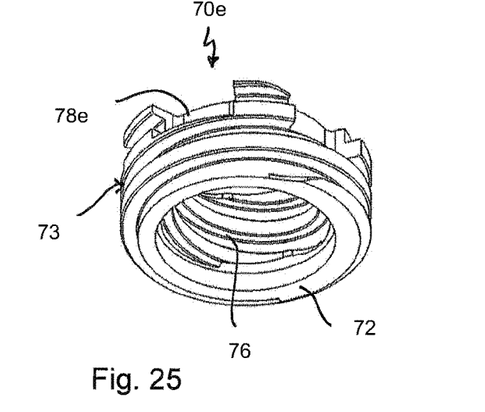
FIG. 25 shows a perspective view from a bottom of the first closure member of FIG. 24.

A fourth embodiment of the closure assembly will be described with reference to FIGS. 5d and 22 to 23. The first closure member 70d differs from the first closure member of the previous embodiments in that the engagement recesses 78d are open only towards the upper end 71 and closed towards the inner surface and towards the outer surface of the first closure member 70d. In other words, the engagement recesses 78d are formed by closed pockets in the upper end 71. The pockets 78d may have a circular segment-shaped or a ring segment-shaped contour with rounded edges or any other shape.

The second locking member 700d differs from the second locking member of the second and third embodiments in that the second locking member 700d is an entirely solid body, where the engagement structure is formed as crossed slots 796d in the upper end 701.

A fifth embodiment of the closure assembly will be described with reference to FIGS. 5e and 24 to 27. The first closure member 70e of the fifth embodiment differs from the first closure member of the previous embodiments in that the engagement structure has a plurality of recesses 78e that are open towards the upper end 71 and towards the outer surface of the first closure member 70e, thereby providing an annular wall 79e at the inner surface of the first closure member 70e. This may result in enhanced stability of the first closure member 70e when the second closure member 700e is tightened. In other words, when the second closure member 700e is tightened, the annular wall 79e may prevent or reduce distortion of the first closure member 70e.

Figure 26:
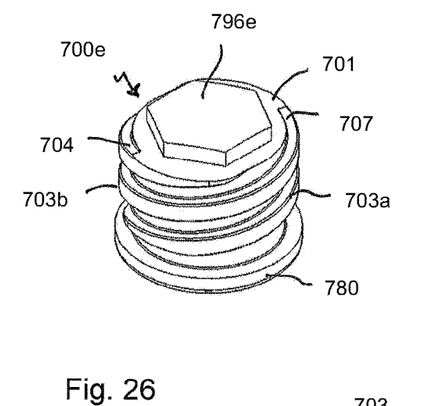
FIG. 26 shows a perspective view from a top of a second closure member of the fifth embodiment of the closure assembly shown in FIG. 5e.
Figure 27:
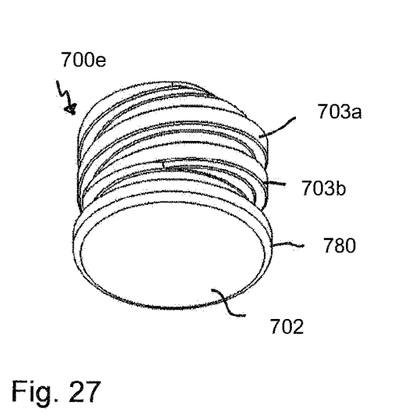
FIG. 27 shows a perspective view from a bottom of the second closure member of FIG. 26.

The second closure member 700e is a solid body and differs from the second closure member 700d of the fourth embodiment in that the engagement structure includes a protrusion 796e provided at the upper end 701. The protrusion 796e may have a polygonal, for example a hexagonal, outer contour.

It shall be noted that the features of the first closure member and the second closure member of any of the first embodiment to the fifth embodiment can be mixed and matched among each other to produce still further embodiments of the closure assembly. Many other shapes of engagement structures for the first and second closure members may also be conceivable.

Figure 28:
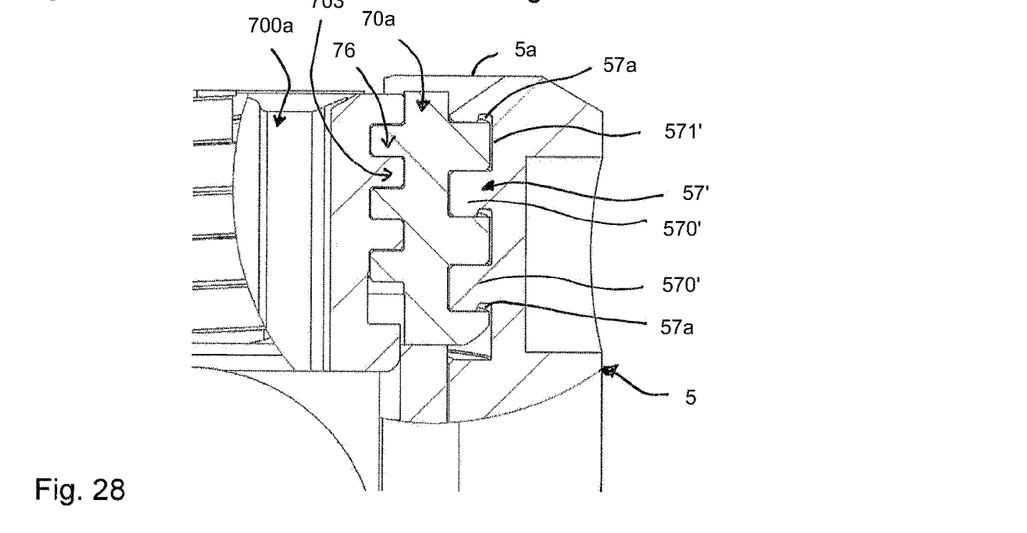
FIG. 28 shows a cross-sectional view of an enlarged portion of the closure assembly of FIG. 5a with a modified embodiment of the bone anchoring device.

Further modifications of the bone anchoring assembly will be described with reference to FIGS. 28 to 30. The modifications relate to the internal thread provided at the legs 55, 56 of the receiving part 5. In a first modification as depicted in FIG. 28, the internal thread 57' differs from the flat thread 57 of the first embodiment in that internal thread 57' can be formed as a helical flange thread. Internal thread 57' includes an undercut portion 57a extending into the lower flank at a region adjacent to the root 571'.

Figure 29:
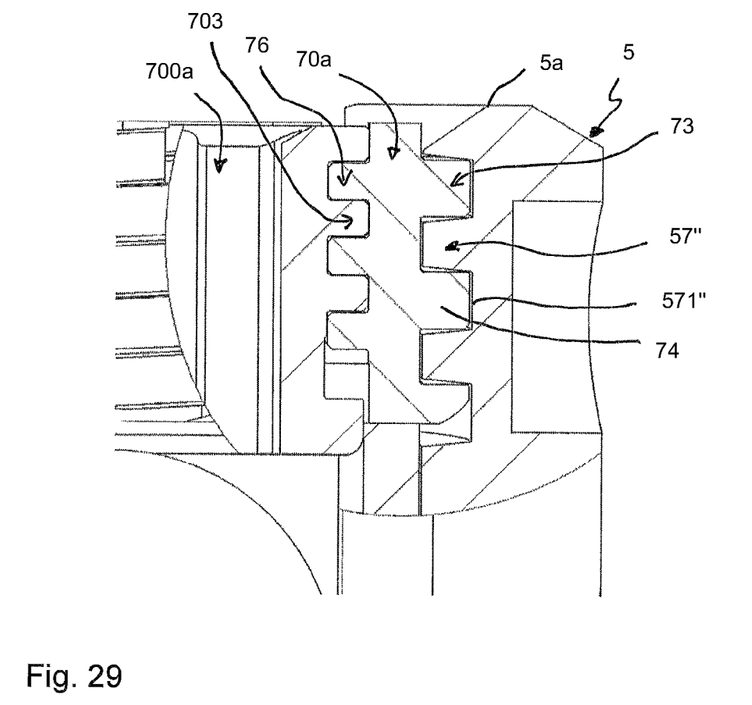
FIG. 29 shows a cross-sectional view of an enlarged portion of the closure assembly of FIG. 5a with a further modified embodiment of the bone anchoring device.

In a further modification, the internal thread 57" of the receiving part can be formed as a trapezoidal thread as shown in FIG. 29. The size of the trapezoidal thread, in particular the width of the root 571" of the trapezoidal thread is such that the thread 57″ permits receipt of the thread ridges 74 of the external thread 73 of the first closure member therein.

Figure 30:
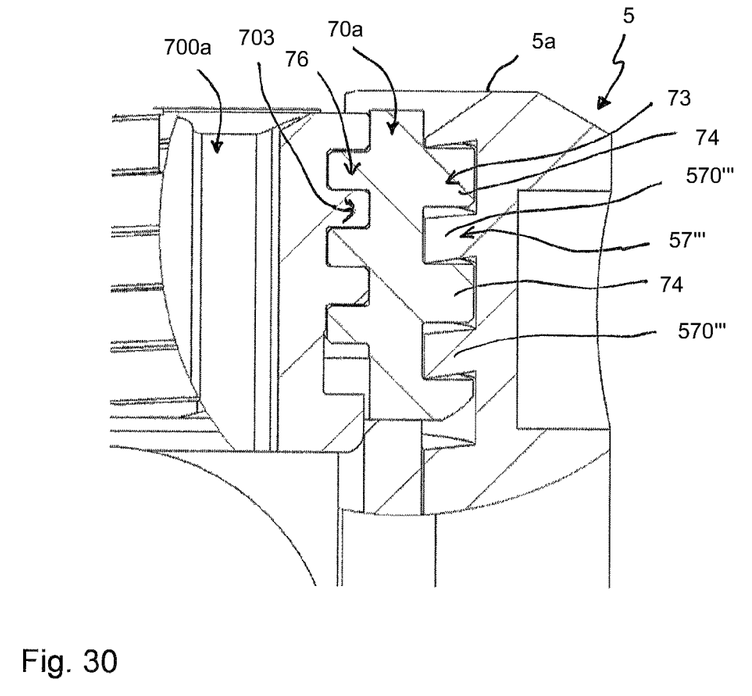
FIG. 30 shows a cross-sectional view of an enlarged portion of the closure assembly of FIG. 5a with a still further modified embodiment of the bone anchoring device.

A further modified embodiment of the receiving part 5 can include a negative angle thread, for example, as shown in FIG. 30. The negative angle thread 57‴ has ridges 570‴ with a lower flank that forms a negative angle with the central axis C. The size of the negative angle thread 57‴ is such that the thread 57‴ permits receipt of the external thread of the first closure member 70a therein.

It shall be noted that various other thread forms can also be used for the internal thread on the receiving part 5, such as a buttress thread, a V-thread (or triangular thread), and others. A thread run-out or an undercut may also be formed in some cases.

The external thread of the first closure member is not limited to a flat thread, but can instead be another thread form that is configured to cooperate with the internal thread of the receiving part.

Also, the thread forms of the internal thread of the first closure member and the external thread of the second closure member are not limited to flat threads. Thread forms such as V-threads, trapezoidal threads, buttress threads, etc. may also be suitable.

Various further modifications of the bone anchoring device and of the closure assembly are also conceivable. While the polyaxial bone anchoring device shown is a specific type of bottom loading polyaxial bone anchoring device, a top loading polyaxial bone anchoring device may also be used. In such a variation, the anchoring element is inserted from the top end into the receiving part. In such an embodiment, the pressure element may be configured to press onto the upper portion of the head, which sits in a seat in the lower portion of the receiving part. Moreover, the shape of the receiving part and/or pressure element are not limited to the embodiments shown. Many other different shapes of receiving part and/or pressure element are also possible. The receiving part and/or the pressure element may each also have, for example, a two-part design.

For the bone anchoring element, all types of bone anchoring elements suitable for anchoring in bone or a vertebra may be used, for example, bone nails. The elongate stabilization element can also be any rod or other stabilization element that is configured to be received between the legs of the receiving part.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A closure assembly for securing an elongate stabilization element in a receiving part of a bone anchoring device, the closure assembly comprising:
   a first closure member receivable between legs of the receiving part, the first closure member having an axis of rotation and comprising an outer surface with a first threaded portion comprising a single-start thread formed on at least a portion thereof that is configured to engage the legs of the receiving part, and an inner surface having at least a portion that is threaded, the inner surface defining a central passage that passes axially through the first closure member; and
   a second closure member having an axis of rotation and an outer surface with a second threaded portion comprising a multi-start thread with at least two starts that are configured to cooperate with the threaded portion of the inner surface of the first closure member.

2. The closure assembly of claim 1, wherein the portion that is threaded on the inner surface of the first closure member comprises a multi-start thread with at least two starts.

3. The closure assembly of claim 1, wherein the second threaded portion of the outer surface of the second closure member comprises a flat thread.

4. The closure assembly of claim 1, wherein the portion that is threaded on the inner surface of the first closure member comprises a flat thread.

5. The closure assembly of claim 1, wherein the second closure member defines an axial passage that extends at least partially through the second closure member and an engagement portion for engagement with a driver.

6. The closure assembly of claim 5, wherein the axial passage extends axially entirely through the second closure member.

7. A bone anchoring device comprising:
   the closure assembly of claim 1; and
   the receiving part comprising two legs defining a U-shaped recess therebetween for receiving the elongate stabilization element.

8. The bone anchoring device of claim 7, wherein the first threaded portion of the outer surface of the first closure member is configured to cooperate with an internal thread formed on the legs of the receiving part.

9. The bone anchoring device of claim 8, wherein the internal thread formed on the legs of the receiving part comprises a single-start thread.

10. The bone anchoring device of claim 8, wherein the first threaded portion comprises a flat thread.

11. The bone anchoring device of claim 8, wherein the internal thread formed on the legs of the receiving part comprises a flat thread, a negative angle thread, a helical flange thread, a trapezoidal thread, or a buttress thread.

12. The bone anchoring device of claim 7, wherein the first closure member has a first end and a second end, and wherein an engagement structure is provided at the first end for engagement with a driver for advancing the first closure member between the legs of the receiving part.

13. The bone anchoring device of claim 12, wherein the engagement structure comprises a plurality of recesses that are open to the first end.

14. The bone anchoring device of claim 13, wherein the recesses of the engagement structure are closed in a radial direction towards the inner surface of the first closure member.

15. The bone anchoring device of claim 13, wherein the recesses of the engagement structure are open in a radial direction towards the outer surface of the first closure member.

16. The bone anchoring device of claim 7, further comprising a shank for anchoring in bone, wherein the shank is pivotably connectable to the receiving part, and wherein the first closure member is configured to lock an angular position of the receiving part relative to the shank and the second closure member is configured to lock the elongate stabilization element in the recess.

17. The bone anchoring device of claim 16, further comprising a pressure element configured to exert pressure onto an inserted head that forms an end portion of the shank, wherein the pressure element comprises a support surface for the elongate stabilization element.

18. The bone anchoring device of claim 17, wherein the support surface for the elongate stabilization element has a substantially V-shaped contour when viewed along a direction perpendicular to the central axis, and wherein sidewalls on either side of the support surface are configured to extend above the elongate stabilization element when the elongate stabilization element is supported on the support surface.

19. A closure assembly for securing an elongate stabilization element in a receiving part of a bone anchoring device, the closure assembly comprising:
   a first closure member receivable between legs of the receiving part, the first closure member having an axis of rotation and comprising an outer surface with an engagement portion configured to engage the legs of the receiving part, and an inner surface having at least a portion that is threaded, the inner surface defining a central passage that passes axially through the first closure member; and
   a second closure member having a first end and an opposite second end, an axis of rotation, and an outer surface with a threaded portion configured to cooperate with the portion that is threaded on the inner surface of the first closure member, wherein the threaded portion of the second closure member comprises a multi-start thread with at least two starts and ends at a distance from the second end, and wherein a radially extending projection is provided at the second end and is configured to abut against a thread turn of the portion that is threaded on the inner surface of the first closure member.

20. A method of coupling an elongate stabilization element to a bone or vertebra using a bone anchoring device comprising a shank for anchoring in the bone or vertebra, a receiving part pivotably connectable to the shank, the receiving part comprising two legs defining a U-shaped recess therebetween for receiving the elongate stabilization element, and a closure assembly for securing the elongate stabilization element in the receiving part, the closure assembly comprising a first closure member receivable between the legs of the receiving part, the first closure member having an axis of rotation and comprising an outer surface with a first threaded portion comprising a single-start thread formed on at least a portion thereof that is configured to engage the legs of the receiving part, and an inner surface having at least a portion that is threaded, the inner surface defining a central passage that passes axially through the first closure member, and a second closure member having an axis of rotation and an outer surface with a second threaded portion comprising a multi-start thread with at least two starts that are configured to cooperate with the threaded portion of the inner surface of the first closure member, the method comprising:
   anchoring the shank to the bone or vertebra;
   adjusting an angular position of the receiving part relative to the shank;
   inserting the elongate stabilization element into the U-shaped recess of the receiving part;
   inserting the closure assembly into the receiving part;
   advancing the first closure member into the receiving part to lock the angular position of the receiving part relative to the shank; and
   advancing the second closure member into the receiving part to lock the elongate stabilization element in the U-shaped recess of the receiving part.

* * * * *